US012070225B2

(12) United States Patent
Kuhn

(10) Patent No.: US 12,070,225 B2
(45) Date of Patent: Aug. 27, 2024

(54) MEDICAL INSTRUMENT FOR TISSUE HEMOSTASIS OR CLOSURE

(71) Applicant: MICRO-TECH (NANJING) CO., LTD., Jiangsu (CN)

(72) Inventor: Daniel Kuhn, Düsseldorf (DE)

(73) Assignee: MICRO-TECH (NANJING) CO., LTD., Jiangsu (CN)

( * ) Notice: Subject to any disclaimer, the term of this patent is extended or adjusted under 35 U.S.C. 154(b) by 540 days.

(21) Appl. No.: 17/441,397

(22) PCT Filed: Apr. 10, 2020

(86) PCT No.: PCT/CN2020/084280
§ 371 (c)(1),
(2) Date: Sep. 21, 2021

(87) PCT Pub. No.: WO2021/004107
PCT Pub. Date: Jan. 14, 2021

(65) Prior Publication Data
US 2022/0167990 A1 Jun. 2, 2022

(30) Foreign Application Priority Data
Jul. 10, 2019 (EP) ..................................... 19185556

(51) Int. Cl.
*A61B 17/128* (2006.01)
*A61B 17/00* (2006.01)
*A61B 17/12* (2006.01)

(52) U.S. Cl.
CPC ............... *A61B 17/1285* (2013.01); *A61B 2017/00477* (2013.01); *A61B 2017/00862* (2013.01); *A61B 2017/12004* (2013.01)

(58) Field of Classification Search
CPC .............. A61B 17/122; A61B 17/128; A61B 17/1285; A61B 17/29; A61B 2017/0034;
(Continued)

(56) References Cited

U.S. PATENT DOCUMENTS 7,094,245 B2 * 8/2006 Adams .................. A61B 90/03
606/139
7,879,052 B2 * 2/2011 Adams ................. A61B 17/122
606/157
(Continued)

FOREIGN PATENT DOCUMENTS

CN      102626335 A      8/2012
CN      102090910 B      12/2012
(Continued)

OTHER PUBLICATIONS

English Abstract for CN109480950 retrieved on Espacenet on Jul. 13, 2021.
(Continued)

*Primary Examiner* — Ryan J. Severson
(74) *Attorney, Agent, or Firm* — BCF LLP

(57) ABSTRACT

Disclosed is a medical instrument, comprising: a protective sheath device; a clamp device comprising a clamp shell arranged on a distal end of the protective sheath device and at least or just two clamp arms; and a control line extending and passing through the protective sheath device, wherein the clamp shell is directly connected to the protective sheath device by means of at least one connection element and is fixedly attached to the clamp shell, or, a portion thereof is releasably connected to the protective sheath device; and a release mechanism cooperating with each connection element is provided, and when the clamp arms have been closed, the release mechanism can be actuated by means of moving the control line in a proximal end direction so as to release each connection element from the protective sheath device and thus release the clamp shell.

23 Claims, 11 Drawing Sheets

(58) Field of Classification Search
CPC .......... A61B 2017/00477; A61B 2017/00862; A61B 2017/12004; A61B 2017/2936

See application file for complete search history.

(56) References Cited

U.S. PATENT DOCUMENTS

| | | | | |
|---|---|---|---|---|
| 8,062,311 | B2* | 11/2011 | Litscher | A61B 17/122 606/143 |
| 8,070,760 | B2* | 12/2011 | Fujita | A61B 17/1227 606/151 |
| 8,858,588 | B2* | 10/2014 | Sigmon, Jr. | A61B 17/08 606/205 |
| 8,915,837 | B2* | 12/2014 | Wells | A61B 17/122 606/139 |
| 9,084,604 | B2* | 7/2015 | Litscher | A61B 17/122 |
| 9,510,836 | B2* | 12/2016 | Zhu | A61B 17/1227 |
| 9,795,390 | B2* | 10/2017 | Jin | A61B 17/1285 |
| 10,172,623 | B2* | 1/2019 | Adams | A61B 17/1285 |
| 10,470,777 | B2* | 11/2019 | Litscher | A61B 17/1285 |
| 10,799,358 | B2* | 10/2020 | Erickson | A61B 17/295 |
| 10,820,904 | B2* | 11/2020 | Ryan | A61B 17/1285 |
| 11,020,125 | B2* | 6/2021 | Randhawa | A61B 17/122 |
| 11,045,194 | B2* | 6/2021 | King | A61B 17/128 |
| 11,160,558 | B2* | 11/2021 | Lehtinen | A61B 17/10 |
| 11,857,213 | B2* | 1/2024 | Nelson | A61B 17/282 |
| 2003/0069592 | A1 | 4/2003 | Adams et al. | |
| 2005/0107809 | A1* | 5/2005 | Litscher | A61B 17/1285 606/142 |
| 2005/0182426 | A1* | 8/2005 | Adams | A61B 17/083 606/213 |
| 2009/0105533 | A1 | 4/2009 | Fujita | |
| 2012/0065647 | A1* | 3/2012 | Litscher | A61B 17/1285 606/143 |
| 2012/0071898 | A1 | 3/2012 | Wells et al. | |
| 2012/0089176 | A1* | 4/2012 | Sigmon, Jr. | A61B 17/10 606/205 |
| 2014/0088616 | A1 | 3/2014 | Clerc et al. | |
| 2014/0171973 | A1 | 6/2014 | Zhu | |
| 2015/0282813 | A1 | 10/2015 | Litscher et al. | |
| 2016/0128698 | A1* | 5/2016 | Adams | A61B 17/083 606/142 |
| 2016/0367258 | A1* | 12/2016 | Jin | A61B 17/1285 |
| 2018/0049745 | A1 | 2/2018 | Randhawa et al. | |
| 2018/0078262 | A1 | 3/2018 | Lehtinen et al. | |
| 2018/0085122 | A1 | 3/2018 | Ryan et al. | |
| 2018/0153552 | A1 | 6/2018 | King et al. | |
| 2019/0053904 | A1 | 2/2019 | Erickson et al. | |
| 2019/0090883 | A1* | 3/2019 | Adams | A61B 17/1227 |
| 2022/0160366 | A1* | 5/2022 | Kuhn | A61B 17/122 |
| 2022/0167990 | A1* | 6/2022 | Kuhn | A61B 17/122 |
| 2022/0202422 | A1* | 6/2022 | Kuhn | A61B 17/122 |

FOREIGN PATENT DOCUMENTS

| | | |
|---|---|---|
| CN | 202699217 U | 1/2013 |
| CN | 202699218 U | 1/2013 |
| CN | 103200883 A | 7/2013 |
| CN | 102626335 B | 4/2014 |
| CN | 103989500 A | 8/2014 |
| CN | 203828993 U | 9/2014 |
| CN | 105935304 A | 9/2016 |
| CN | 206239447 U | 6/2017 |
| CN | 107115130 A | 9/2017 |
| CN | 206482631 U | 9/2017 |
| CN | 107684448 A | 2/2018 |
| CN | 108635007 A | 10/2018 |
| CN | 109009310 A | 12/2018 |
| CN | 109199515 A | 1/2019 |
| CN | 208435704 | 1/2019 |
| CN | 109480950 A | 3/2019 |
| CN | 109805977 A | 5/2019 |
| CN | 209884245 U | 1/2020 |
| EP | 1328199 A1 | 7/2003 |
| EP | 1829489 A1 | 9/2007 |
| EP | 2371303 A1 | 10/2011 |
| EP | 2380509 A2 | 10/2011 |
| EP | 3053532 A1 | 8/2016 |
| EP | 3081174 A1 | 10/2016 |
| EP | 1328199 B1 | 6/2018 |
| WO | 95/11620 A2 | 5/1995 |
| WO | 2008070486 A2 | 6/2008 |
| WO | 2011/022246 A1 | 2/2011 |
| WO | 2012/051191 A2 | 4/2012 |
| WO | 2018/235402 A1 | 12/2018 |

OTHER PUBLICATIONS

European Search Report and Opinion with regard to EP19169940.4 completed Dec. 3, 2019.
European Search Report and Opinion with regard to EP19169946.1 completed Oct. 15, 2019.
Nsternational Search Report (including Translation) and Writte Opinion with regard to PCT/CN2020/085337 completed Jun. 23, 2020.
Partial European Search Report with regard to EP19169940 completed Oct. 8, 2019.
English Abstract for CN109009310 retrieved on Espacenet on Jul. 13, 2021.
English Abstract for CN107684448 retrieved on Espacenet on Sep. 22, 2021.
English Abstract for CN105935304 retrieved on Espacenet on Jul. 13, 2021.
English Abstract for CN102090910 retrieved on Espacenet on Sep. 22, 2021.
International Search Report (including English Translation) and Written Opinion with regard to PCT/CN2020/084497 mailed Jun. 29, 2020.
English Abstract for CN202699217 retrieved on Espacenet on Sep. 27, 2021.
English Abstract for CN202699218 retrieved on Espacenet on Sep. 27, 2021.
English Abstract for CN206239447 retrieved on Espacenet on Sep. 27, 2021.
English Abstract for CN206482631 retrieved on Espacenet on Sep. 27, 2021.
English Abstract for CN109199515 retrieved on Espacenet on Sep. 27, 2021.
International Search Report (including English Translation) and Written Opinion with regard to PCT/CN2020/084280 mailed Jun. 23, 2020.
English Abstract for CN109805977 retrieved on Espacenet on Jul. 13, 2021.
English Abstract for CN209884245 retrieved on Espacenet on Jul. 13, 2021.
English Abstract for CN103989500 retrieved on Espacenet on Jul. 13, 2021.
English Abstract for CN203828993 retrieved on Espacenet on Jul. 13, 2021.
European Search Report and Opinion with regard to EP19185556.8 completed Jan. 7, 2020.
English Abstract for CN108635007 retrieved on Espacenet on Sep. 20, 2021.
English Abstract for CN208435704 retrieved on Espacenet on Jul. 13, 2021.
English Abstract for CN107115130 retrieved on Espacenet on Jul. 13, 2021.
English Abstract for CN103200883 retrieved on Espacenet on Jul. 13, 2021.
English Abstract for CN102626335 retrieved on Espacenet on Jul. 13, 2021.

* cited by examiner

MEDICAL INSTRUMENT FOR TISSUE HEMOSTASIS OR CLOSURE

CROSS-REFERENCE TO RELATED APPLICATIONS

The present application is a National Stage of International Application No. PCT/CN2020/084280, filed on Apr. 10, 2020, which claims priority to European Patent Application No. EP19185556.8, filed with the European Patent Office on Jul. 10, 2019, entitled "Medical Device for Causing the Hemostasis of a Blood Vessel", each of which is incorporated herein by reference in its entirety.

TECHNICAL FIELD

The present disclosure relates to the field of medical devices and in particular to a medical device for hemostasis or closure of tissues.

BACKGROUND ART

Medical devices of this kind are known in the prior art for example from EP1328199B1 and in particular used to treat gastrointestinal bleedings. Specifically, such devices are used to set clamps or clips to pinch a bleeding vessel, applying sufficient constrictive force to the blood vessel, so as to limit or interrupt blood flow therethrough.

The medical device known from EP1328199B1 comprises a handle and a sheath, which is attached to the handle. A control wire extends through the sheath and can be actuated by an actuator, which is coupled to the proximal end of the control wire to reversibly move the control wire in the distal and proximal directions. The medical device further includes a clamp device including a sleeve provided on the distal end of the sheath and a clip with two clamp arms is coupled to the distal end of the control wire by means of a J-hook. The clamp arms cooperate with the sleeve in such a way, that the clamp arms engage the front edge of the sleeve to be elastically deformed inwardly, thus being closed, when the control wire is pulled in the proximal direction, whereas the clamp arms are distally pushed out of the sleeve and automatically reopen due to their elastic restoring force, when the control wire is pushed in the distal direction. Since the clamp device can be repeatedly opened and closed, setting of the clamp device is possible in an easy way.

Once the clamp device is set at the correct position, the clamp device with the clamp arms and the sleeve can be disconnected from the rest of the medical device. In order to do so the control wire is further pulled back, when the clamp device is completely closed, so that the J-hooks break and thus the connection between the clamp arms and the control wire is interrupted. Moreover, by further pulling back the control wire a retainer which connects the control wire with the sleeve is actuated, in order to disconnect the retainer and thus the control wire from the sleeve.

SUMMARY

In order to solve at least one of the technical problems in the prior art, the object of the present disclosure includes providing a medical device of the above mentioned kind that is easy to operate as well as easy to manufacture and assemble.

An embodiment of the present disclosure provides a medical device for hemostasis or closure of tissues, said medical device comprising:
a handle;
a sheath device, which is attached to the handle;
a clamp device, including a clamp housing with a clamp base and at least or exactly two clamp arms, wherein the clamp base is in particular in the form of a sleeve provided on the distal end of the sheath device;
a control wire, extending through the sheath device and configured to be reversibly movable in the distal and proximal directions; and
an actuator, coupled to the proximal end of the control wire and configured to be actuable to reversibly move the control wire in the distal and proximal directions,
wherein the clamp arms are each coupled to the distal end of the control wire, and wherein the clamp device is configured to be actuable to open and close the clamp arms by a movement of the control wire, such that a movement of the control wire in the proximal direction is translated into a closing movement of the clamp arms and a movement of the control wire in the distal direction is translated into an opening movement of the clamp arms.

Optionally, the clamp housing is directly connected to the sheath device by at least one connecting element,
each connecting element is fixedly attached to or part of the clamp housing and releasably connected to the sheath device, and
a release arrangement cooperating with each connecting element is provided and can be actuated by moving the control wire in the proximal direction when the clamp arms have been closed, to release each connecting element and thus the clamp housing from the sheath device.

Optionally, the clamp housing and the sheath device are directly connected to each other by according connecting elements, which are fixedly provided on or parts of the clamp housing and releasably connected to the sheath device. In this way a very reliable and stable connection between the clamp housing and the sheath device is obtained. Also, the medical device according to the present disclosure is simple in design and easy to manufacture.

The connecting elements can be actuated in order to release the clamp base from the sheath device, when the clamp arms have been closed. Specifically, the arrangement is such that when the clamp arms have been closed and the control wire is moved further in the proximal direction the clamp housing is released from the sheath device.

According to an optional embodiment of the present disclosure, the sheath device comprises a sheath, optionally an extendable coiled sheath, and a connect tube provided on the distal end of the sheath. Optionally, the connect tube is connected to the sheath in such a way that the connect tube can be rotated relative to the sheath around its central longitudinal axis. For this purpose, a ring groove may be provided in the outer circumferential surface of the connect tube. Engagement members are then fixedly provided on and optionally welded to the sheath, which engage into the ring groove in order to connect/couple the connect tube to the sheath. In this coherence the engagement members may engage with a ring shoulder in the ring groove.

Optionally, at least two connecting elements are provided and located with a regular angular offset along the outer circumference of the clamp housing, wherein, optionally, exactly two connecting elements are provided and located on opposite sides of the clamp housing.

An optional embodiment of the present disclosure provides, that the connecting elements are provided in the form of resilient, elastically deformable connecting arms, wherein the distal ends of the connecting elements are fixedly attached to the clamp housing and the free proximal ends of the connecting elements form engagement portions that engage corresponding engagement means of the sheath device in order to connect the clamp housing to the sheath device, and that the release arrangement comprises a protrusion, that is arranged between and cooperates with the connecting elements in such a way, that the protrusion presses against the connecting elements elastically deforming them outwardly, so that the engagement portions of the connecting elements are urged outwardly into engagement with the corresponding engagement means of the sheath device, in order to connect the clamp housing to the sheath device, wherein the protrusion is coupled with and in particular fixedly provided on the control wire in such a way, that if after closing the clamp arms the control wire is moved further in the proximal direction the protrusion is moved together with the control wire out of engagement from the connecting elements with the result that the latter are deformed inwardly by their elastic restoring force and the engagement portions of the connecting elements come out of engagement of the corresponding engagement means of the sheath device to release the clamp housing from the sheath device.

Optionally, the connecting elements are provided with bulged sections, which are in particular provided at the free end of the connecting elements, and the protrusion is arranged between and cooperated with the bulged sections of the connecting elements to deform the connecting elements outwardly, wherein the connecting elements are deformed inwardly by their elastic restoring force when the protrusion is moved out of engagement from the bulged sections.

Optionally, the engagement portions of the elastic connecting elements are actively held in engagement with the engagement means provided in the clamp base by the engagement of the protrusion and the connecting elements (in particular the bulged sections of the connecting elements). Once this engagement is no more existent, because the control wire is pulled back in the proximal direction so far, that the protrusion is no more arranged/located between the connecting elements/the bulged sections, the connecting elements are elastically deformed inwardly by their restoring force. In other words, the connection between the sheath device and the clamp base is passively released by moving the protrusion of the control wire out of the range of the connecting elements or bulged sections thereof.

An optional embodiment of the present disclosure provides that the clamp housing is connected to the sheath device by a push-in connection thus forming an overlapping section, wherein, optionally, the proximal end of the clamp housing is inserted into the distal end of the sheath device, and that the engagement means are provided as recesses or through-holes in the inner circumferential wall of the sheath device, wherein, preferably, the engagement portions of the connecting elements are formed as outwardly directed connecting fingers.

Optionally, the engagement means of the sheath device and corresponding apertures are provided in the overlapping section of the sheath device and the clamp housing such that the engagement portions of the connecting elements are pressed outwardly through the apertures in the clamp housing into the engagement means of the sheath device in order to connect the clamp housing to the sheath device.

The connecting elements may have a straight section, which is slanted inwardly with regard to a central longitudinal axis of the clamp housing if viewed in the proximal direction, wherein the slanting angle is in particular 3° to 15° and optionally 5°.

According to an optional embodiment of the present disclosure, the connecting elements are fixedly connected to the clamp housing at the distal end section thereof, wherein, in particular, the distal ends of the connecting elements are directed radially outwardly and extend out into corresponding holding apertures provided in the clamp housing and are optionally fixed therein by welding.

Optionally, the clamp housing comprises two bearing arms extending in the distal direction from the clamp base and the connecting elements are fixedly attached to the bearing arms at the free end sections thereof, wherein, in particular, a guide pin is held between the two bearing arms and the connecting elements are provided on the distal side of the guide pin.

An optional embodiment of the present disclosure provides that the clamp arms are coupled to the control wire by means of a pivot pin which is provided at the distal end section of the control wire and extends through corresponding through-holes provided in the tail ends of the clamp arms, and that exit-passages are provided in the tail ends of the clamp arms at the proximal side of the through-holes, through which after closing the clamp arms the pivot pin can be pulled out of the through-holes and from the clamp arms spreading apart the tail end sections of the clamp arms on the opposite sides of the exit-passages without breaking them by a proximal movement of the control wire in order to uncouple the control wire from the clamp arms.

Optionally, the clamp arms are directly coupled to the control wire, thus omitting the necessity to provide for a separate coupling element for example in the form of a J-hook. Specifically, the control wire is provided at its distal end section with a pivot pin, which engages corresponding through-holes provided in the proximal end sections of the clamp arms.

The through-holes are open to the proximal end of the clamp arms. Specifically exit-passages are provided which are designed such, that they are small enough, so that the pivot pin cannot fall out of the clamp arms unintentionally, but can be intentionally pulled out of the through-holes through the exit-passages by exerting a sufficiently high tensile force to the control wire, so that the tail end sections of the clamp arms on the opposite side of the exit-passages are spread apart and thus deformed.

The exit-passages may for example be formed by slits in the tail ends of the clamp arms.

According to an optional embodiment of the present disclosure, the tail end sections of the clamp arms are elastically or plastically deformed, when they are spread apart. In any way the arrangement is such that the tail end sections do not break in order to avoid, that parts of the breakable arms remain freely in the body of a patient.

An optional embodiment of the present disclosure provides that the tail end sections of the clamp arms on the opposite sides of the exit passages engage behind at least one shoulder of the clamp base in order to lock the clamp arms to the clamp base. Optionally, the tail end sections of the clamp arms on the opposite sides of the exit-passages form hooks that engage behind the at least one shoulder of the clamp base in order to lock the clamp arms to the clamp base.

The shoulder can be formed by an annular projection of the clamp base, wherein the annular projection in particular forms the distal end face of the clamp base with a central opening, through which the tail ends of the clamp arms extend into the clamp base when the clamp arms are fully closed.

If the tail end sections on the opposite side of the exit-passages of the clamp arms are plastically deformed, when the pivot pin is pulled out of engagement from the clamp arms, provision is made, that the proximal ends of the clamp arms are positioned behind, i.e., on the proximal side of the shoulder of the clamp base so that the clamp arms are plastically deformed to engage behind the shoulder lock the clamp arms to the clamp base and consequently the clamp arms cannot be removed from the clamp base anymore. In this way further separate locking elements are not necessary.

According to an optional embodiment of the present disclosure, a coupling head is provided at the distal end of the control wire and the pivot pin is provided on the coupling head. Optionally, the coupling head includes a U-shaped holding structure opened to its distal side, wherein the clamp arms are partly arranged between the legs of the U-shaped holding structure and the pivot pin is held between the legs of the U-shaped holding structure and extends through the through-holes of the clamp arms. In particular, the clamp arms may extend laterally outwards of the open lateral side of the U-shaped holding structure. In this embodiment the clamp arms are arranged in the U-shaped holding structure and may therefore be in direct contact with each other.

According to an optional embodiment of the present disclosure, the object is solved by a medical device of the initially mentioned kind, which is characterized in that the clamp device includes exactly two clamp arms which are provided as separate elements, that are each coupled to the distal end of the control wire in a pivotal manner around a common pivot axis defined by a pivot pin, wherein each clamp arm is provided with a guide groove and the guide grooves of the clamp arms partially overlap each other, and a guide pin which is attached to the clamp housing and extends through the guide grooves in the overlapping parts thereof, so that by the engagement of the guide pin and the guide grooves a movement of the control wire in the proximal direction is translated into a closing movement of the clamp arms and a movement of the control wire in the distal direction is translated into an opening movement of the clamp arms around the pivot axis.

Optionally, the clamp arms are separate elements/components that are not directly connected to one another. Instead, the clamp arms are each coupled to the control wire by the engagement of their through-holes with the pivot pin. Moreover, the clamp arms are coupled by the engagement of the guide pin and the guide grooves to the clamp housing in such a way, that an axial movement of the control wire is translated into closing/opening movements of the clamp arms around the pivot axis. According to an optional embodiment, the guide pin is held between two bearing arms of the clamp housing extending in the distal direction from the clamp base, in particular at the free end sections of the bearing arms. In this case the connecting elements may be provided on the proximal side of the guided pin.

Optionally, holding noses are provided on the clamp arms which extend into the guide grooves from a lateral side thereof and are designed in such a way, that they allow the guide pin to pass them to reach the distal ends of the guide grooves but prevent passing of the guide pin in the opposite direction. In particular, the guide grooves may have straight, axially extending distal end section, in which the guide pin can move without incurring rotation of the clamp arms and the holding noses extend into the straight end sections. In particular, recesses may be formed in the lateral sides of the guide grooves on the distal side of the holding nose, into which the holding noses are elastically deformed to allow the guide pin to pass the holding noses and reach its distal end positions in the guide grooves.

Optionally, the guide pin is captured in the distal ends of the guide grooves by means of the holding noses, thus locking the clamp to the clamp base. In this way further locking elements are no more necessary.

BRIEF DESCRIPTION OF THE DRAWINGS

Embodiments of the present disclosure will in the following be described making reference to the attached drawings. In these drawings

Figure 1:
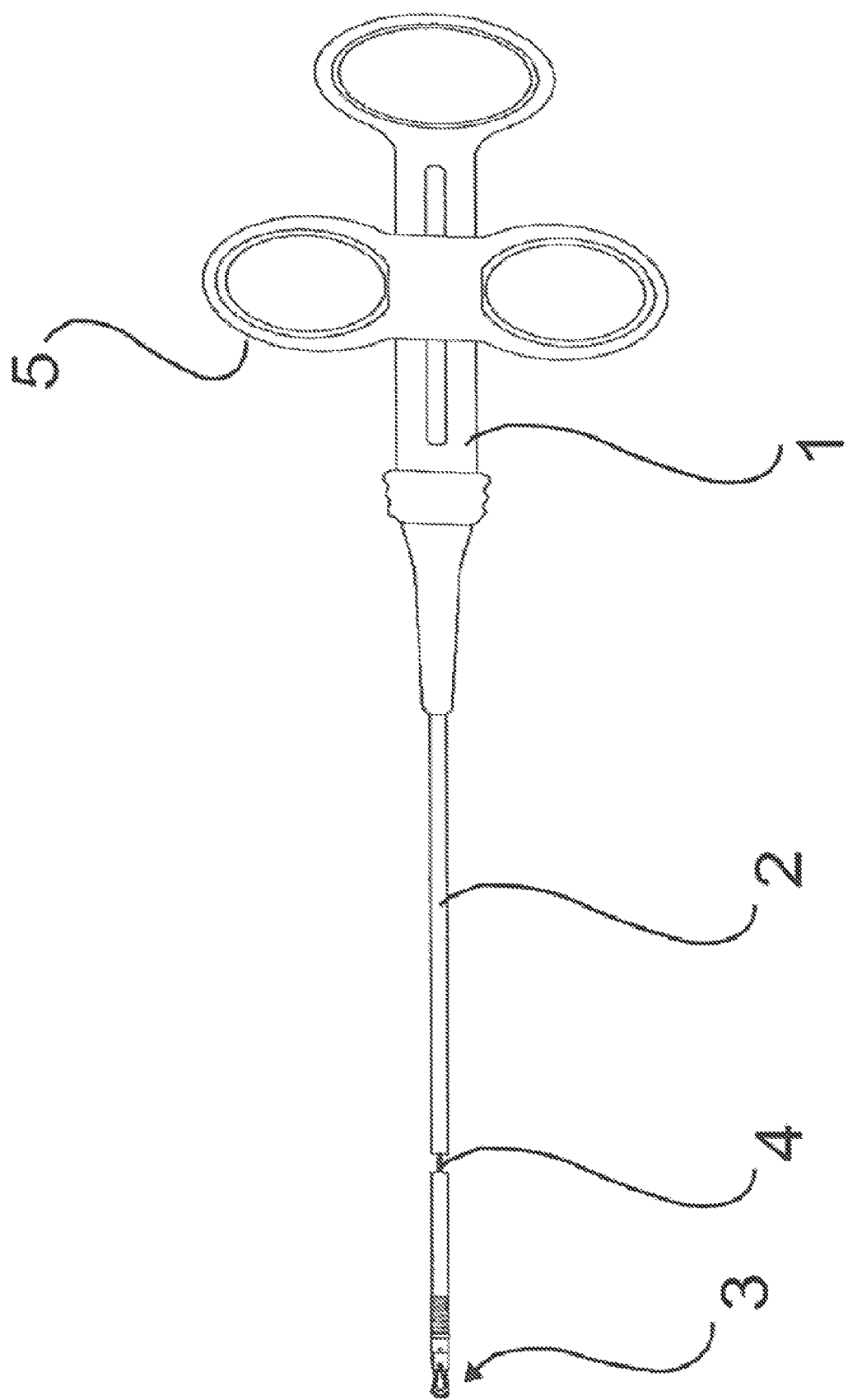
FIG. 1 shows a front view of a medical device according to an embodiment of the present disclosure.
Figure 2:
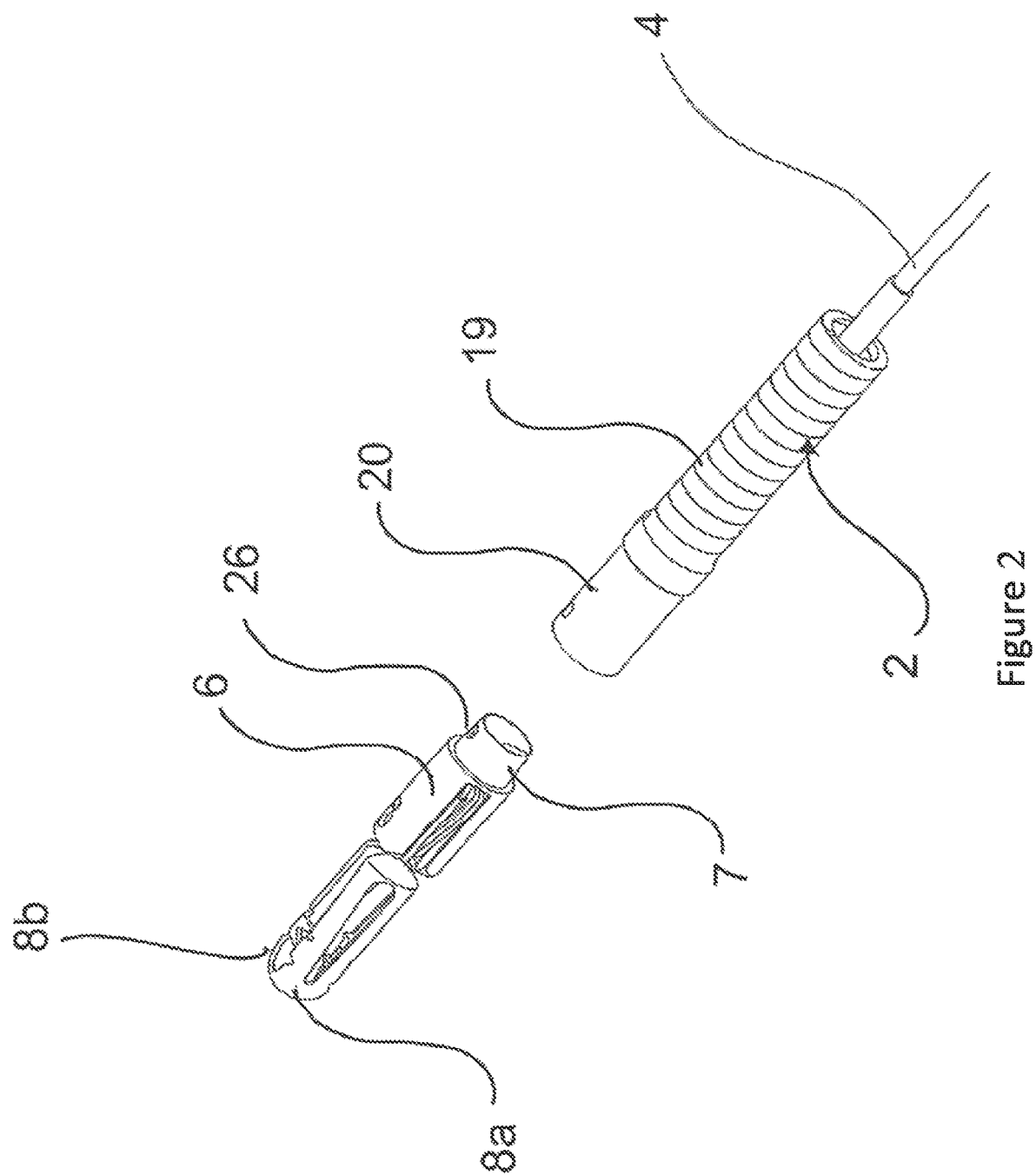
FIG. 2 shows in enlarged scale the front, distal part of the medical device of FIG. 1 in partially sectioned view, with the clamp device separated from the sheath device.

Reference Numerals: 1—handle; 2—sheath device; 3—clamp device; 4—control wire; 5—actuator; 6—clamp housing; 7—clamp base; 8a, 8b clamp arm; 9—pivot pin; 10—through-hole; 11—coupling head; 12—guide groove; 12a—distal end section; 12b—recess; 13—guide pin; 14a, 14b—bearing arm; 15—exit-passage; 16, 17—tail end section; 18—shoulder; 19—sheath; 20—connect tube; 21—ring groove; 22—engagement member; 23—connecting element; 24—engagement portion; 25—engagement means; 26—apertures; 27—holding aperture; 28—straight section; 29—bulged section; 30—protrusion; 31—holding nose

DETAILED DESCRIPTION OF THE EMBODIMENTS

In FIGS. 1 to 13 an embodiment of a medical device according to the present disclosure is shown. The medical device is used to set clamps for causing hemostasis of blood vessels located along the gastrointestinal tract, wherein the clamps are delivered to a target site through an endoscope.

As shown in FIG. 1, the medical device comprises a handle 1, a sheath device 2, which is attached to the handle 1, and a clamp device 3 which is provided on the distal end of the sheath device 2. A control wire 4 extends through the sheath device 2 and is at its proximal end connected to an actuator 5, which is slidingly held on the handle 1 and can be actuated to reversibly move the control wire 4 in the distal and proximal directions.

Figure 3:
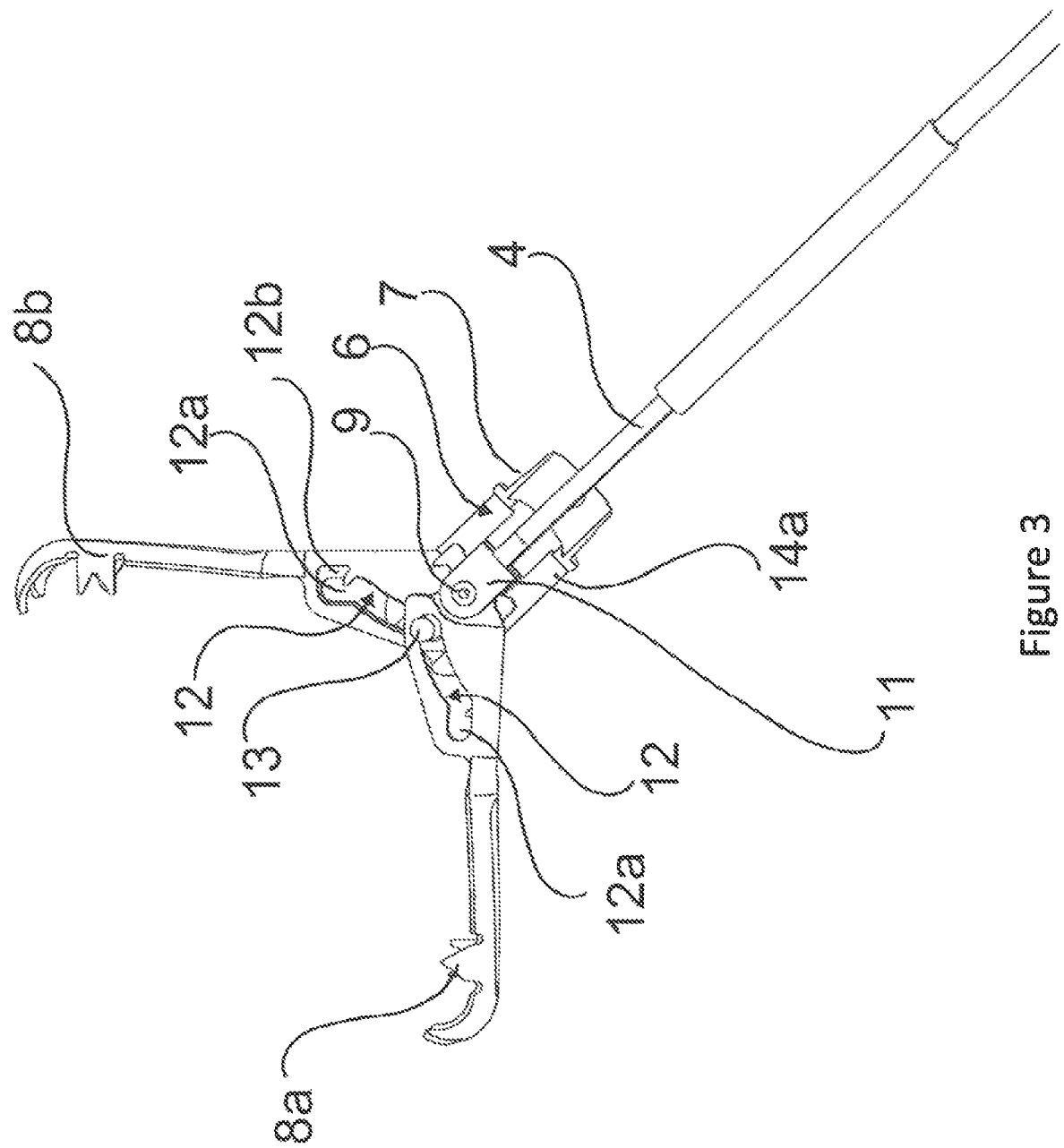
FIG. 3 is a partially sectioned view of the clamp device with the clamp arms in fully open state.
Figure 4:
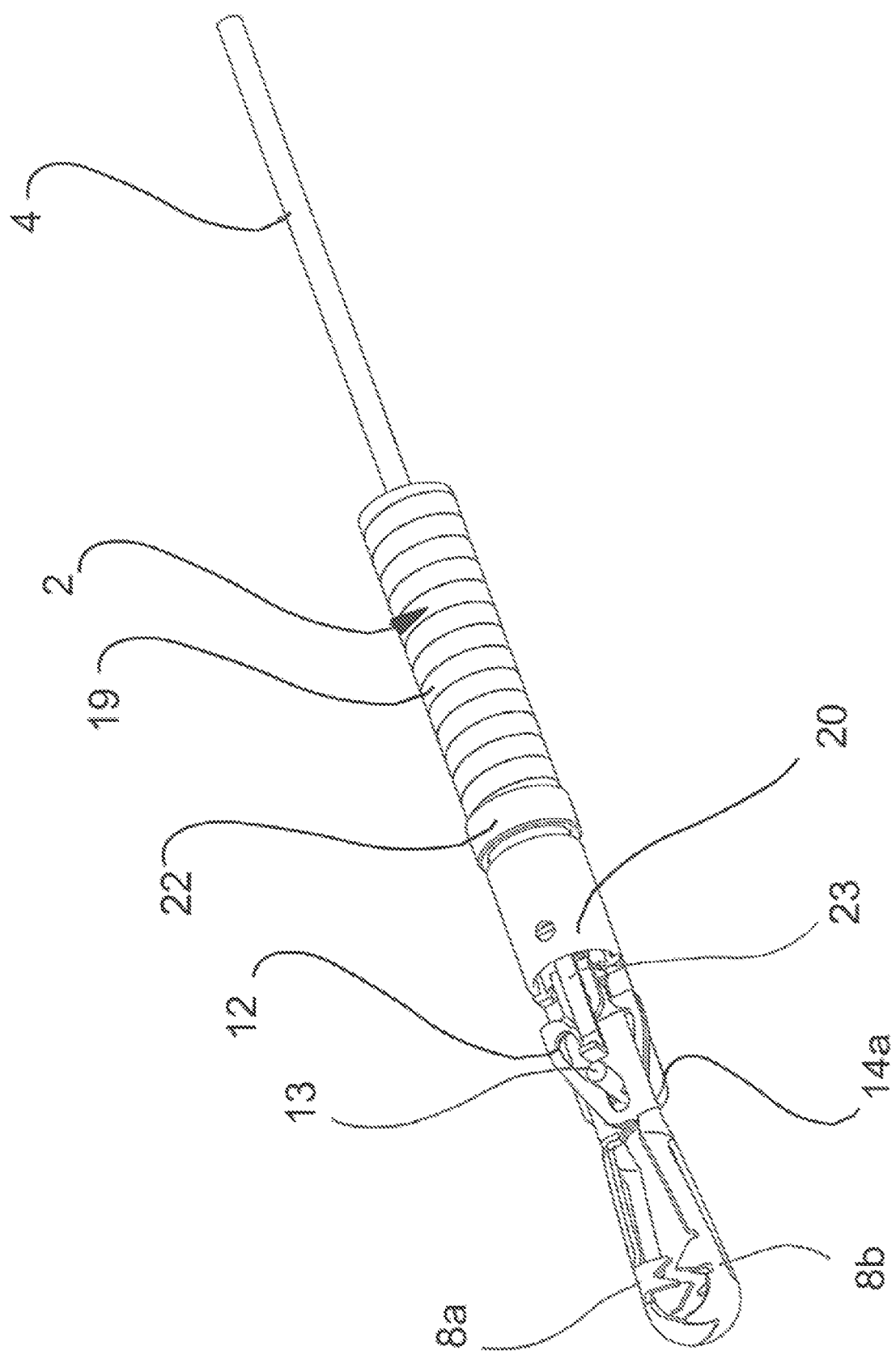
FIG. 4 is a partially sectioned view of the clamp device with closed clamp arms, FIG. 5 corresponds to FIG. 4 and shows the clamp device with the clamp arms in fully closed and secured position, FIG. 6 corresponds to FIGS. 5 and shows the process of uncoupling the control wire from the clamp arms.

As shown in FIG. 3, the clamp device 3 comprises a clamp housing 6 with a clamp base 7 formed as a sleeve and two clamp arms 8a, 8b, which are each coupled to the distal end of the control wire 4. Specifically, the two clamp arms 8a, 8b are separate elements/components that are coupled to the control wire 4 by means of a pivot pin 9, which is provided at a distal end section of the control wire 4 and extends through corresponding through-holes 10 provided in the proximal end sections of the clamp arms 8a, 8b. In the present embodiment the pivot pin 9 is provided on a coupling head 11, which is provided at the distal end of the control wire 4.

Figure 8:
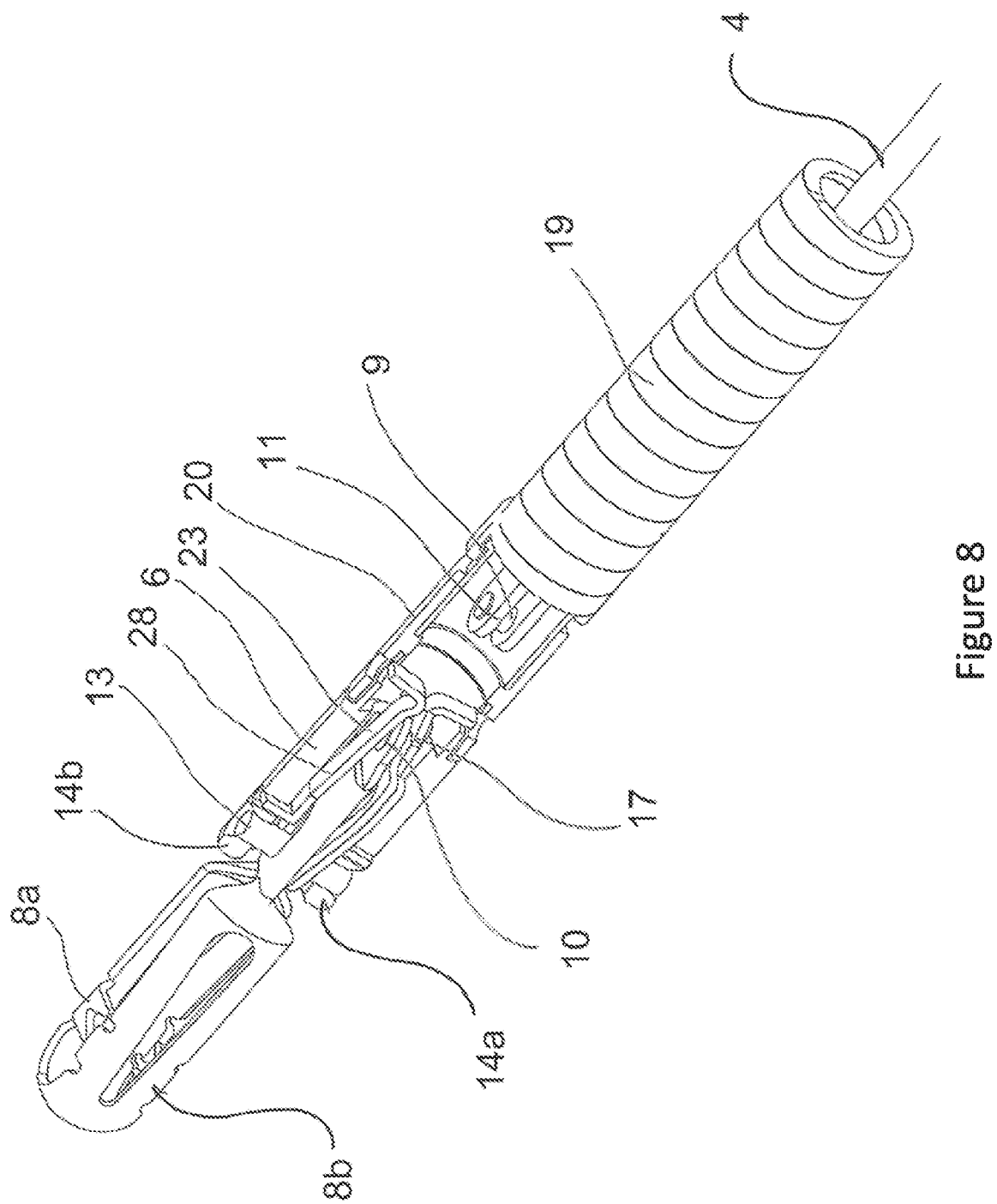

As shown in FIG. 8, the coupling head 11 has a U-shaped or bifurcated holding structure which is open on its distal end, and the clamp arms 8a, 8b are partly arranged between the legs of the U-shaped holding structure. The pivot pin 9 is held between the legs of the U-shaped holding structure and extends through the through-holes 10 of the clamp arms 8a, 8b, which in turn extend laterally outwards of or laterally protrudes from the open lateral side of the U-shaped holding structure.

As shown in FIGS. 5 to 7 and FIG. 11, the two clamp arms 8a, 8b are coupled to the distal end of the control wire 4 so that they can be rotated around a common pivot axis formed by the pivot pin 9 in order to open and close them. Each clamp arm 8a, 8b is provided with a guide groove 12, and the guide grooves 12 of the clamp arms 8a, 8b partially overlap each other.

The clamp device 3 further comprises a guide pin 13, which is attached to the clamp housing 6 and extends through the guide grooves 12 in the overlapping parts thereof, so that by the engagement of the guide pin 13 and the guide grooves 12 a movement of the control wire 4 in the proximal direction is translated into a closing movement of the clamp arms 8a, 8b, and a movement of the control wire 4 in a distal direction is translated into an opening movement of the clamp arms 8a, 8b around the pivot axis. In the present embodiment the guide pin 13 is held between two bearing arms 14a, 14b of the clamp housing 6 extending upright from the distal end of the clamp base 7 forming a bifurcated structure, the clamp arms 8a, 8b being arranged between those bearing arms 14a, 14b extending laterally outward of the structure.

Figure 9:
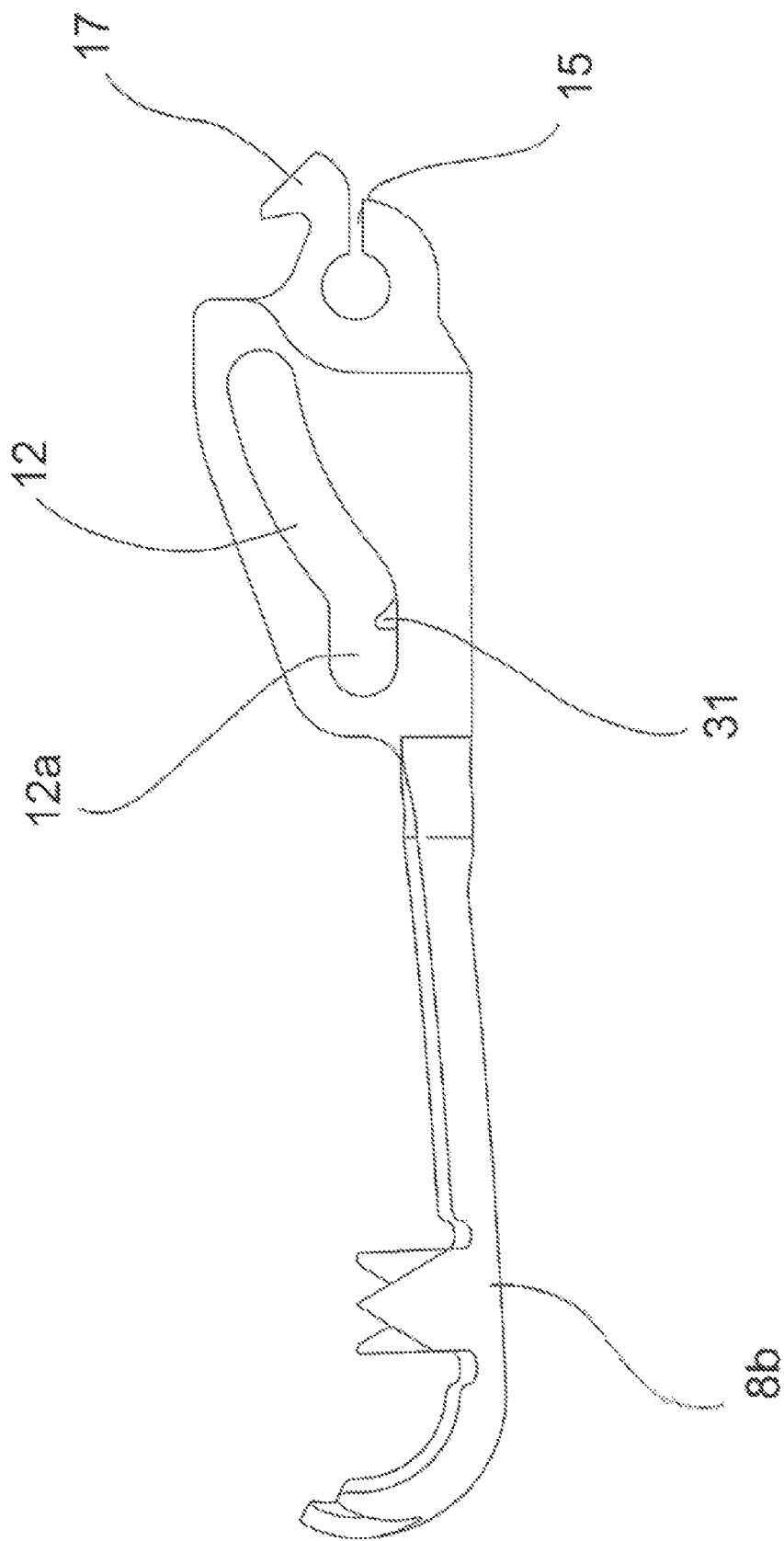
FIG. 9 is a front view of a clamp arm of the clamp device.

As in particular shown in FIG. 9 the through-holes 10 for the pivot pin 9 in the proximal end sections of the clamp arms 8a, 8b are open to their rear (proximal) side. In other words, exit-passages 15 are provided in the tail ends of the clamp arms 8a, 8b at the proximal sides of the through-holes 10, through which after closing the clamp arms 8a, 8b the pivot pin 9 can be pulled out of the through-holes 10 spreading apart the tail end sections 16, 17 of the clamp arms 8a, 8b on the opposite sides of the openings without breaking them. In this way the control wire 4 is uncoupled from the clamp arms 8a, 8b and accordingly the clamp device 3. The exit-passages 15 are here formed by slits in the tail ends of the clamp arms 8a, 8b.

The tail end sections 16, 17 of the clamp arms 8a, 8b are plastically deformed, when they are spread apart, one tail end section 16 is formed as a hook, which is to be brought into engagement behind a shoulder 18 of the clamp base 7 in order to lock the clamp arms 8a, 8b therein, as will be explained in detail later. The shoulder 18 is formed by an annular, inwardly directed projection that is provided at the distal end of the clamp base 7 and forms the distal end face thereof.

Figure 5:
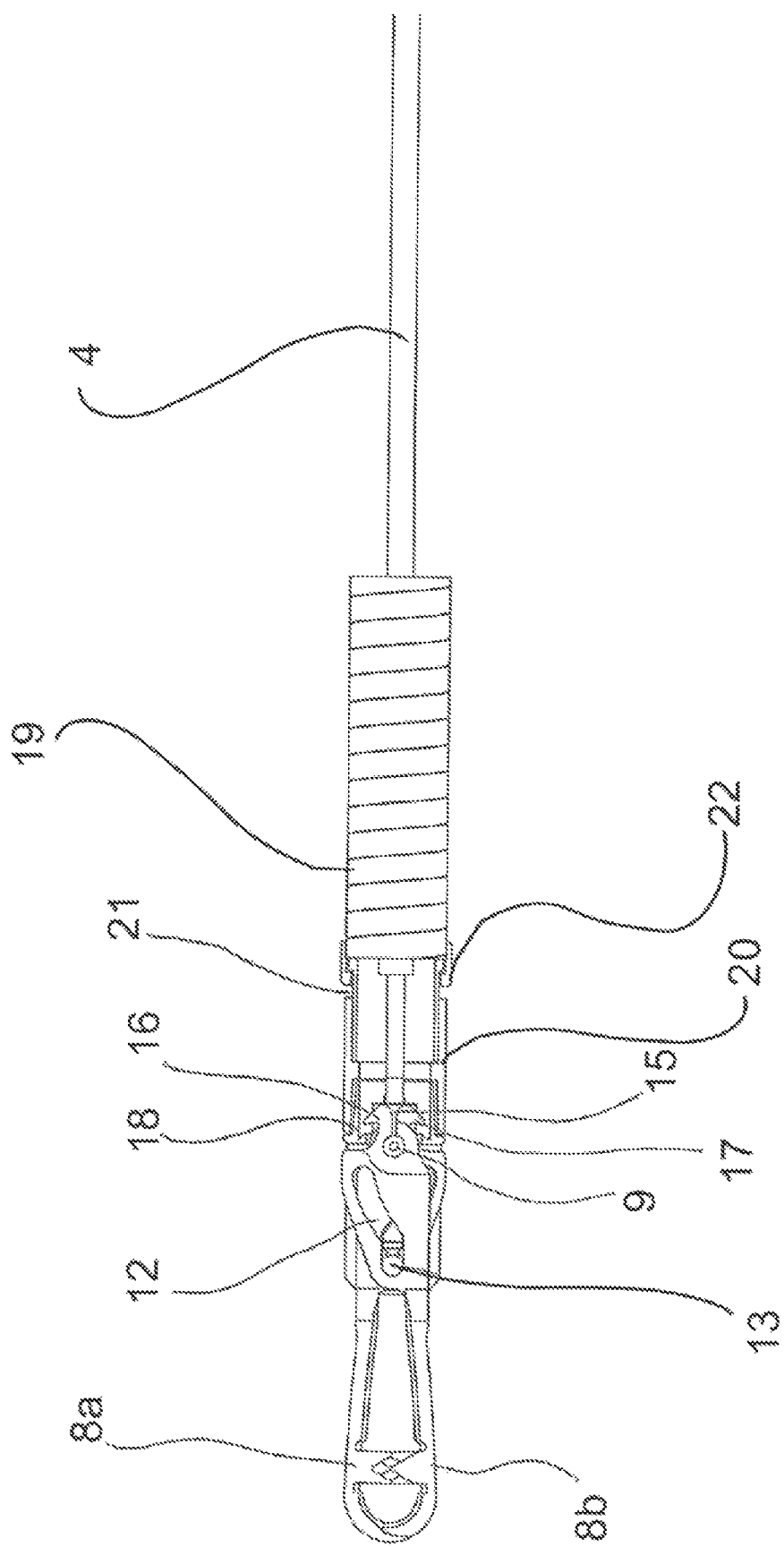
Figure 6:
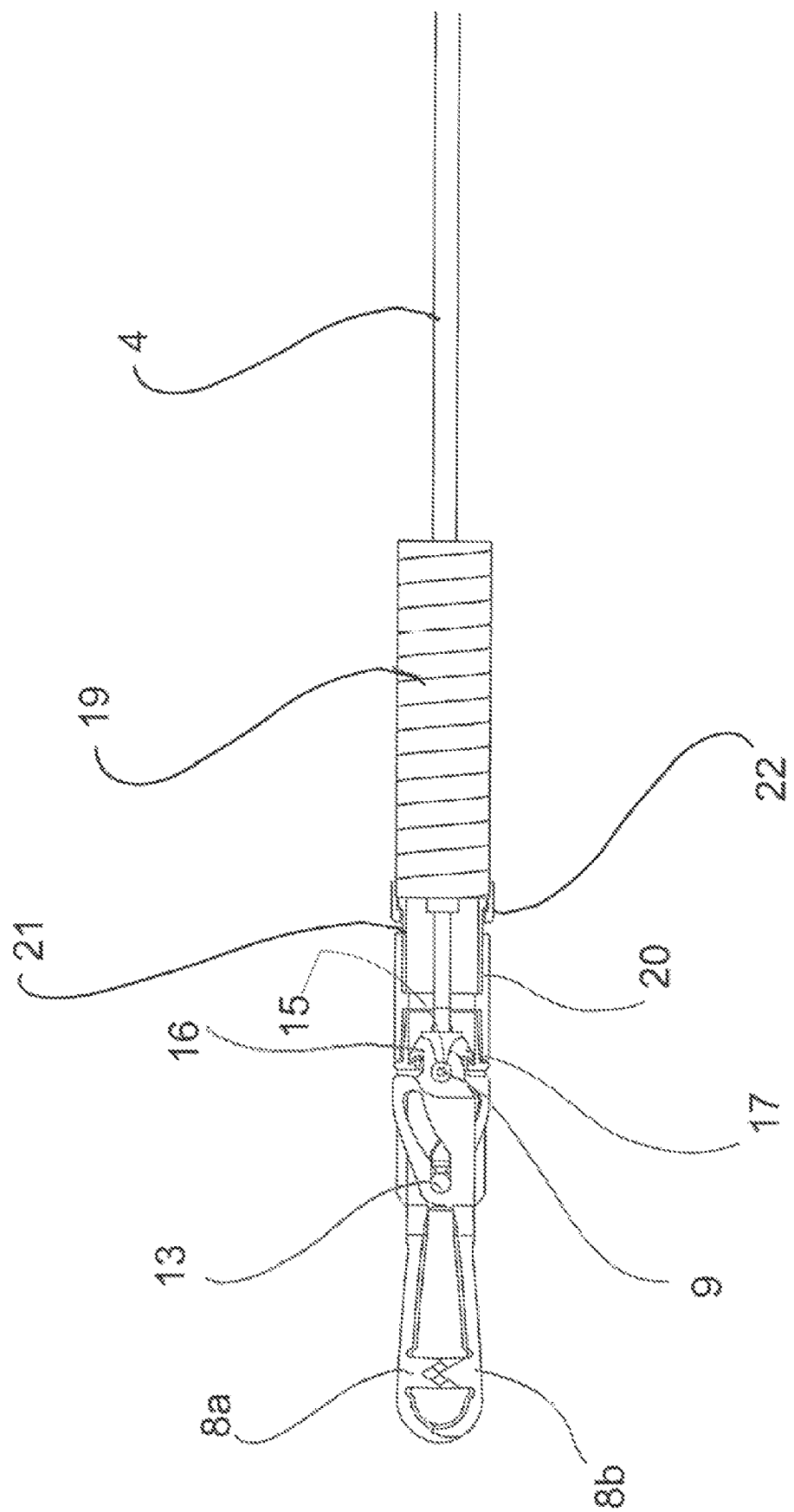
Figure 7:
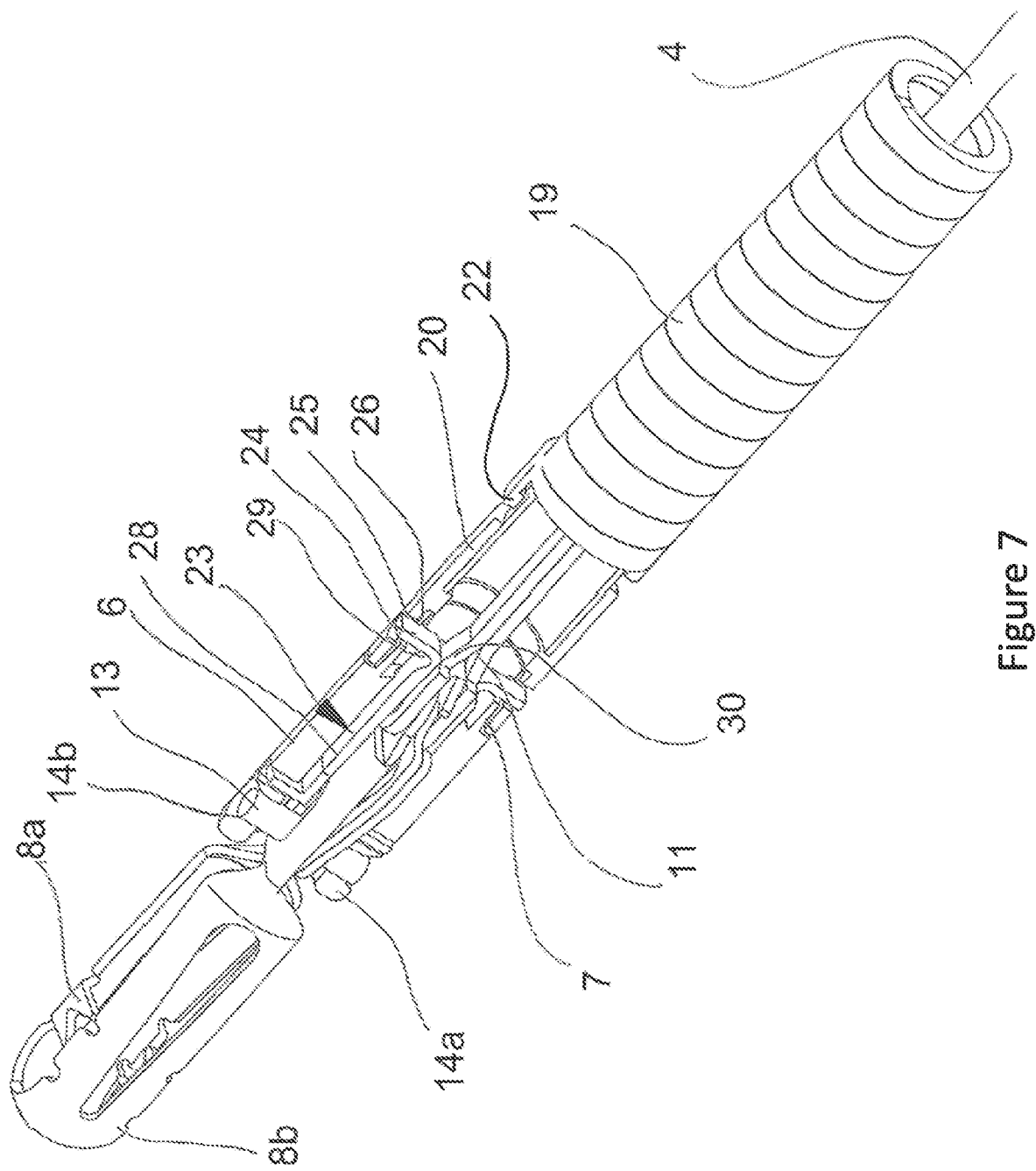
FIGS. 7 and 8 are a partially sectioned view of the distal part of the medical device showing the release of the clamp housing from the sheath device.

As shown in FIGS. 5 to 7, the sheath device 2 includes a coiled sheath 19, which is connected to the handle 1, and a connect tube 20, which is provided on the distal end of the coiled sheath 19, so that the sheath device 2 forms an inseparable unit. The connect tube 20 is connected to the sheath 19 in such a way, that the connect tube 20 can be freely rotated relative to the sheath 19 around its central longitudinal axis. For this purpose, a ring groove 21 is provided in the outer circumferential surface of the connect tube 20 and engagement members 22 are fixedly provided on and optionally welded to the sheath 19, which engage into the ring groove 21 in order to connect the tube 20 rotatable to the sheath 19. In the present embodiment the engagement members 22 are formed as ring members provided on a holding sleeve, which is welded to the sheath 19. Here, the ring groove 21 mentioned above is in fact also a separate ring member having a ring-shaped projection at its distal tail end, which is also referred to as a shoulder in the present disclosure. Correspondingly, projections are also provided at the proximal tail ends of the engagement members 22. The relationship of the engagement of the abovementioned two kinds of projections allows the connect tube 20 to be rotated relative to the sheath 19 around its central longitudinal axis while being fixed and unmovable in its length direction after it is connected to the sheath 19.

Figure 12:
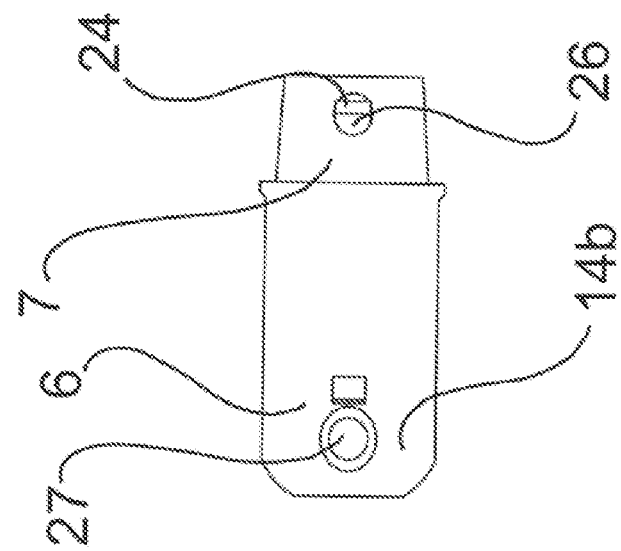
Figure 11:
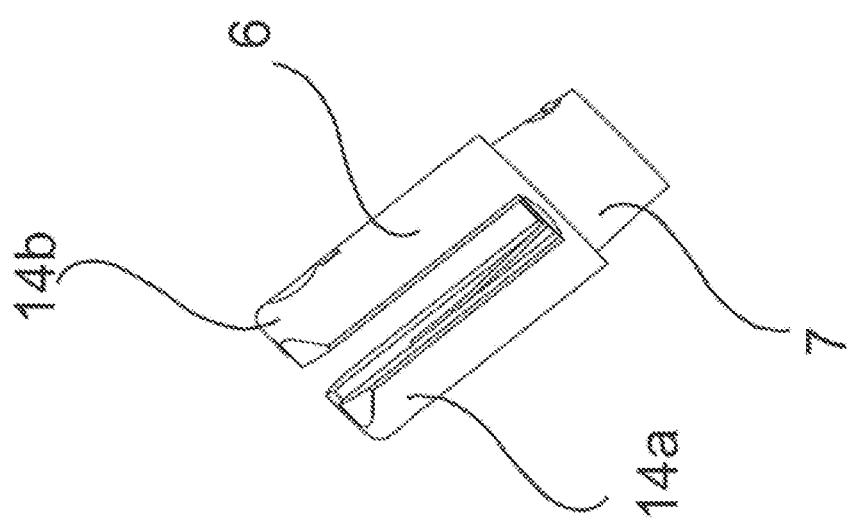
FIG. 11 is a perspective view of the clamp housing.

As shown in FIGS. 7 and 8, the sheath device 2 is connected to the clamp housing 6 by means of two connecting elements 23 in the form of elastic connecting arms that are positioned on opposite sides of the clamp housing 6. Specifically, the distal ends of the connecting elements 23 are fixedly attached to the clamp housing 6, whereas the free proximal ends of the connecting elements 23 form engagement portions 24 that engage corresponding engagement means 25 provided in the inner circumferential surface of the connect tube 20, in order to couple the clamp housing 6 to the sheath device 2. Here, the clamp housing 6 is connected to the sheath device 2 by a push-in connection, wherein the proximal end of the clamp housing 6 is inserted/extends into the distal end of the connect tube 20 of the sheath device 2. As shown in FIG. 12, in the overlapping sections of the connect tube 20, the engagement means 25 of the sheath device 2 are provided in the form of through-holes, and apertures 26 corresponding to the through-holes are provided in the clamp housing 6 such that the engagement portions 24 of the connecting elements 23 are pressed outwardly through the apertures 26 and the clamp housing 6 into the engagement means 25 of the sheath device 2 in order to connect the clamp housing 6 to the sheath device 2.

Figure 13:
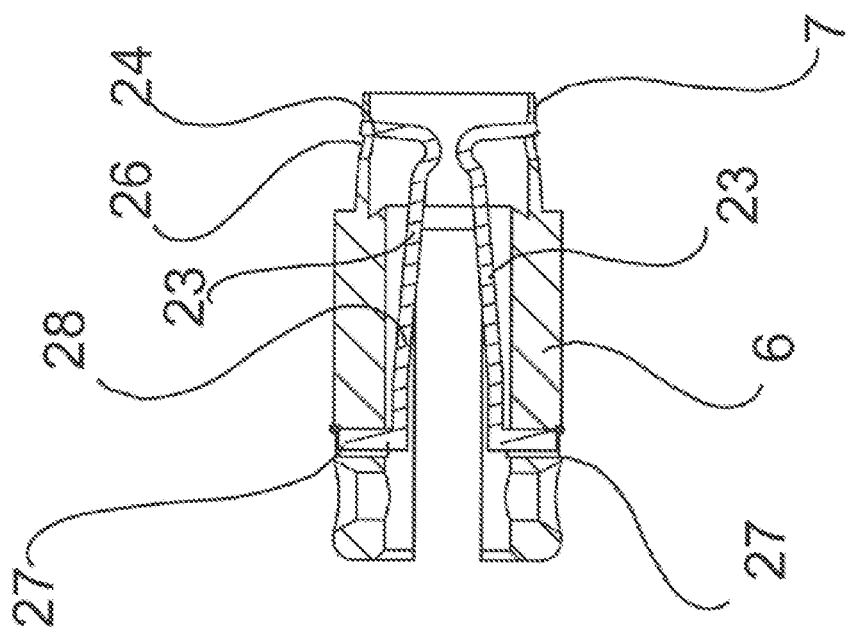
FIG. 12 is a front view of the clamp housing and FIG. 13 is a sectioned view of the clamp housing.

As shown in FIG. 13, the connecting elements 23 have inwardly bulged sections. Further, the distal ends of the connecting elements 23 are directed radially outwardly and extend into corresponding holding apertures 27 provided in the clamp housing 6, and are optionally fixed therein by welding. The connecting elements 23 further have a straight section 28 following the distal end of the connecting elements 23, which is slanted inwardly with regard to the central longitudinal axis of the clamp housing if use in the proximal direction, wherein the slanting angle is 5°. Between the straight section 28 and the engagement portions 24 of the connecting elements 23 an inwardly bulged section 29 is provided at the proximal end of the connecting elements 23.

Figure 10:
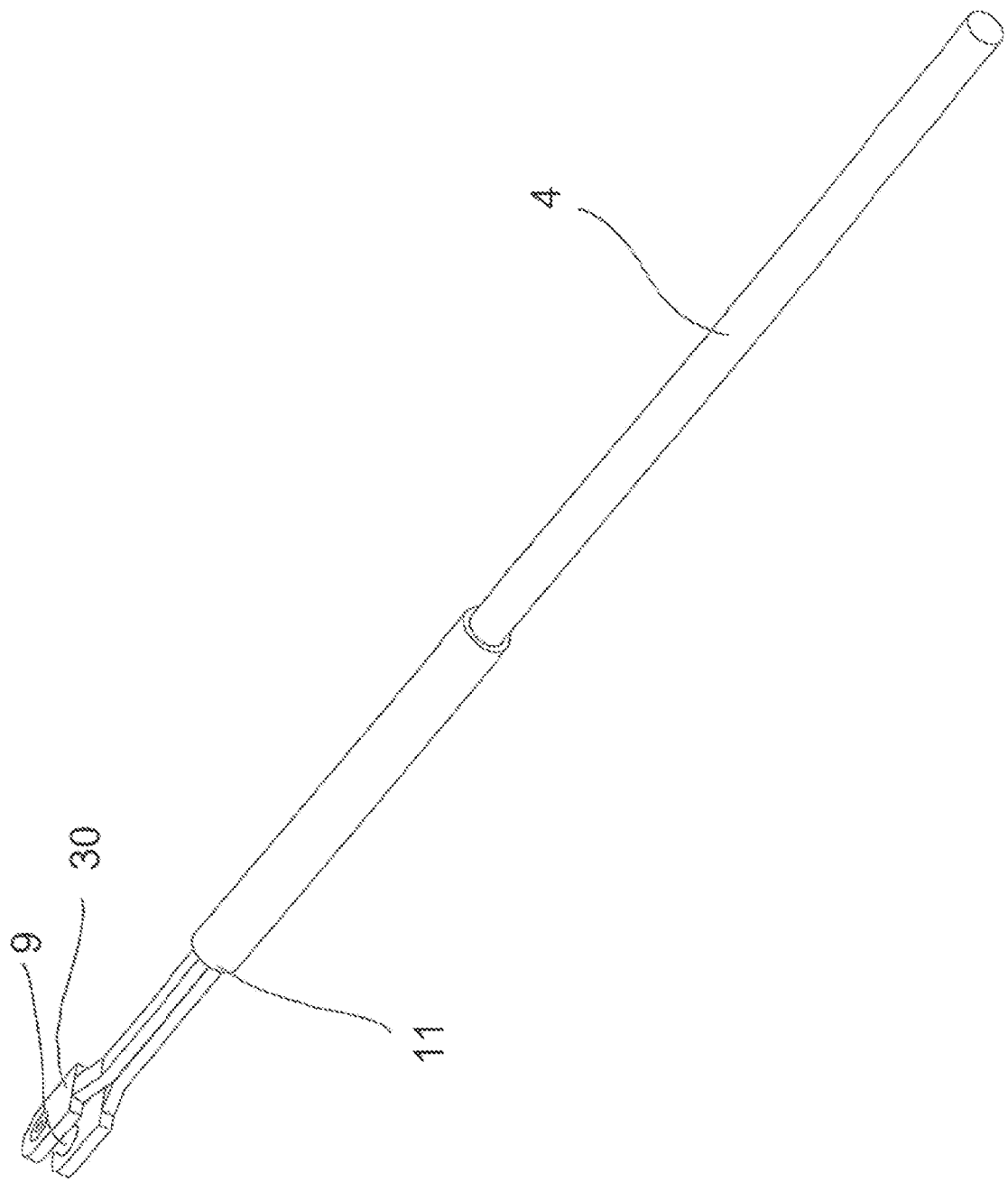
FIG. 10 is a perspective view of the control wire with the protrusion and the coupling head.

As shown in FIG. 10, in an embodiment, a release arrangement for disconnecting the clamp housing 6 from the connect tube 20 is provided. This release arrangement comprises a protrusion 30 provided on the control wire 4. The protrusion 30 cooperates with and is located between the inwardly bulged sections 29 of the connecting elements 23 to press the inwardly bulged sections 29 outwardly elastically deforming the connecting elements 23 in such a way that their free ends are pressed. When the control wire 4 is pulled proximally and the protrusion 30 comes out of engagement of the connecting elements 23, the bulged sections 29 are re-deformed inwardly by their elastic restoring force to obtain their original shape and the connecting portions 24 come out of engagement of the engagement means 25 of the connect tube 20.

In use, the clamp device 3 is delivered to the target site through an endoscope, and the clamp device 3 is fixed at a predetermined position on the target site to a blood vessel. In order to pinch the blood vessel, the clamp arms 8a, 8b can be repeatedly opened and closed by moving the control wire 4 in the distal and proximal direction by means of the actuator 5.

Once the clamp device 3 has been set, the clamp arms 8a, 8b are to be disconnected from the control wire 4. For this purpose, the control wire 4 is pulled in proximal direction in order to fully close the clamp arms 8a, 8b and secure them in the closed position, as depicted in FIG. 9. This figure shows, that the guide grooves 12 have a straight, axially extending distal end section 12a, in which the guide pins 13 can move without incurring further rotation of the clamp arms 8a, 8b. When the guide pin 13 reaches the distal end positions in the guide grooves 12, it is secured/locked in this position by holding noses 31 provided on the clamp arms 8a, 8b. The holding noses 31 extend into the straight end sections 12a of the guide grooves 12 from a lateral side thereof and are designed in such a way, that they allow the guide pin 13 to pass them to reach the proximal ends of the guide grooves 12 but prevent passing of the guide pin 13 in the opposite direction. Specifically the holding noses 31 are designed such that they elastically deform into recesses 12b in the lateral sides of the guide grooves 12 when the guide pins 13 press against their proximal side to allow the guide pin 13 to pass the holding noses 31 and reach its distal end position in the guide grooves 12, that they regain their initial form by their elastic restoring force to engage behind the guide pin 13, when the guide pin 13 has reached its final position, but that they cannot be deformed to reopen the guide grooves 12 when the guide pin 13 presses against their distal sides, so that the guide pins 13 are captured in their distal end positions in the guide grooves 12. In this way the clamp arms 8a, 8b are securely locked to the clamp base 7 and accordingly to the clamp housing 6.

If the control wire 4 is further pulled back, a further movement of the clamp arms 8a, 8b is no more possible, and insofar the pivot pin 9 is pulled out of the through-holes 10 through the exit-passages 15 on the rear side thereof. During this process the tail end sections 16, 17 of the clamp arms 8a, 8b located on the opposite side of the exit-passages 15 are plastically spread apart to open the exit-passages 15.

In order to uncouple/release the clamp housing 6 from the sheath device 2, the control wire 4 is further pulled back in proximal direction, so that the protrusion 30 of the coupling head 11 comes out of engagement from the inwardly bulged sections 29 of the connecting elements 23 so that the connecting elements 23 regain the initial shape in which their free ends come out of engagement from the engagement means 25 of the connect tube 20 of the sheath device 2.

During the closing process of the clamp arms 8a, 8b the tail ends of the clamp arms 8a, 8b enter the clamp base 7 through the central opening of the ring-shaped shoulder 18 so that they engage behind the shoulder 18 of the clamp base 7 in order to lock the clamp arms 8a, 8b to the clamp base 7.

Optionally, as shown in FIGS. 2 to 9, in the medical device according to each embodiment of the present disclosure, the clamp arms 8a, 8b of the clamp device 3 may be provided with at least two toothlike members, which are referred hereinafter to as lateral teeth. Optionally, the lateral teeth are formed integrally with the corresponding clamp arms 8a, 8b. Here, each lateral tooth has a tooth top and a tooth bottom, and each clamp arm has the same number of lateral teeth. Optionally, the lateral teeth on the clamp arm 8a on one side are positioned symmetrically but shaped oppositely (or complementarily) to the lateral teeth on the clamp arm 8b on the other side. For example, as shown in FIGS. 11 to 20 of the present disclosure, the at least two lateral teeth on each clamp arm are distributed on the two sides of the clamp arm in its axial direction (i.e., length direction) and are located at the same positions and have opposite tooth shapes. Here, the clamp arm 8a on one side is taken as an example. As shown in the figures, in the axial direction of this clamp arm, the tooth on the left side is a male tooth and the tooth on the right side is a female tooth. Thus, the clamp arm 8b on the other side can be exactly obtained by turning the clamp arm 8a on one side around its axis by 180 degrees. Such design for the clamp arms 8a, 8b of the clamp device 3 according to the present disclosure enables that the clamp arms on both sides can be manufactured by using one mold, whereby the manufacture process is simplified and the product cost is reduced. The above-mentioned lateral teeth provided on the clamp arms enable the medical device to grasp biological tissues more securely and thus allow a safer and more controllable operation when it is used for clinical hemostasis or wound closure.

INDUSTRIAL APPLICABILITY

The present disclosure discloses a medical device that is easy to operate as well as easy to manufacture and assemble. In the medical device according to the present disclosure, the clamp housing and the sheath device are directly connected to each other by corresponding connecting elements, which are fixedly provided on the clamp housing or a part thereof and releasably connected to the sheath device. In this way, a very reliable and stable connection between the clamp housing and the sheath device is obtained, enabling that the medical device of the present disclosure is simple in design and easy to manufacture.

What is claimed is:
1. A medical device for hemostasis or closure of tissues, said medical device comprising:
a handle;
a sheath device, which is attached to the handle;
a clamp device, comprising at least or exactly two clamp arms and a clamp housing with a clamp base, wherein in particular, the clamp base is in a form of a sleeve provided on a distal end of the sheath device, and;
a control wire, extending through the sheath device and configured to be reversibly movable in distal and proximal directions; and
an actuator, coupled to a proximal end of the control wire and configured to be actuable to reversibly move the control wire in the distal and proximal directions,
wherein the clamp arms are each coupled to a distal end of the control wire and wherein the clamp device is configured to be actuable to open and close the clamp arms by a movement of the control wire such that a movement of the control wire in the proximal direction is translated into a closing movement of the clamp arms and a movement of the control wire in the distal direction is translated into an opening movement of the clamp arms;

wherein the clamp housing is directly connected to the sheath device by at least one connecting element, each of the at least one connecting element is fixedly attached to the clamp housing or a part of the clamp housing and releasably connected to the sheath device, and a release arrangement, configured to cooperate with the each of the at least one connecting element, is provided and the release arrangement is configured for being able to be actuated by moving the control wire in the proximal direction when the clamp arms have been closed, to release the each of the at least one connecting element and thus the clamp housing from the sheath device.

2. The medical device according to claim 1, wherein the sheath device comprises a sheath, and further a connect tube provided on a distal end of the sheath.

3. The medical device according to claim 2, wherein the sheath is an extendable coiled sheath.

4. The medical device according to claim 3, wherein the connect tube is connected to the sheath in such a way that the connect tube can be rotated relative to the sheath around its central longitudinal axis.

5. The medical device according to claim 4, wherein a ring groove is provided in the outer circumferential surface of the connect tube and engagement members are fixedly provided on the sheath, which engage into the ring groove in order to connect the connect tube to the sheath.

6. The medical device according to claim 5, wherein the engagement members are welded to the sheath, and the engagement members engage with a ring shoulder in the ring groove.

7. The medical device according to claim 1, wherein at least two connecting elements are provided and located with a regular angular offset along an outer circumference of the clamp housing.

8. The medical device according to claim 7, wherein exactly two connecting elements are provided and located on opposite sides of the clamp housing.

9. The medical device according to claim 8, wherein the connecting elements are provided in a form of resilient, elastically deformable connecting arms, wherein distal ends of the connecting elements are fixedly attached to the clamp housing and free proximal ends of the connecting elements form engagement portions that engage corresponding engagement means of the sheath device in order to connect the clamp housing to the sheath device, and the release arrangement comprises a protrusion, that is arranged between and cooperates with the connecting elements in such a way that the protrusion presses against the connecting elements to make the connecting elements elastically deform outwardly, so that the engagement portions of the connecting elements are urged outwardly into engagement with the corresponding engagement means of the sheath device, in order to connect the clamp housing to the sheath device, wherein the protrusion is coupled with and in particular fixedly provided on the control wire in such a way that if after closing the clamp arms the control wire is moved further in the proximal direction, the protrusion is moved together with the control wire out of engagement from the connecting elements with a result that the connecting elements are deformed inwardly by their elastic restoring force and the engagement portions of the connecting elements come out of engagement of the corresponding engagement means of the sheath device to release the clamp housing from the sheath device.

10. The medical device according to claim 9, wherein the connecting elements are provided with bulged sections, which are in particular provided at free ends of the connecting elements, and the protrusion is arranged between the bulged sections of the connecting elements and configured to be cooperated with the bulged sections to deform the connecting elements outwardly, wherein the connecting elements are deformed inwardly by their elastic restoring force when the protrusion is moved out of engagement from the bulged sections.

11. The medical device according to claim 9, wherein the clamp housing is connected to the sheath device by a push-in connection thus forming an overlapping section, and the engagement means are provided as recesses or through-holes in an inner circumferential wall of the sheath device.

12. The medical device according to claim 11, wherein a proximal end of the clamp housing is inserted into a distal end of the sheath device, and the engagement portions of the connecting elements are formed as outwardly directed connecting fingers.

13. The medical device according to claim 12, wherein the engagement means of the sheath device and corresponding apertures are provided in the overlapping section of the sheath device and the clamp housing such that the engagement portions of the connecting elements are pressed outwardly through the apertures in the clamp housing into the engagement means of the sheath device in order to connect the clamp housing to the sheath device.

14. The medical device according to claim 9, wherein the connecting elements have a straight section, which is slanted inwardly with regard to a central longitudinal axis of the clamp housing if viewed in the proximal direction, wherein the slanting angle is in particular 3° to 15° and preferably 5°.

15. The medical device according to claim 9, wherein the connecting elements are fixedly connected to the clamp housing at the distal end section thereof.

16. The medical device according to claim 15, wherein the distal ends of the connecting elements are directed radially outwardly and extend out into corresponding holding apertures provided in the clamp housing and are fixed therein by welding.

17. The medical device according to claim 16, wherein the clamp housing comprises two bearing arms extending in the distal direction from the clamp base and the connecting elements are fixedly attached to the bearing arms at free end sections thereof, wherein, in particular, a guide pin is held between the two bearing arms and the connecting elements are provided on the proximal side of the guide pin.

18. The medical device according to claim 1, wherein each of the clamp arms is provided with at least two lateral teeth, wherein the at least two lateral teeth on the clamp arm on either side are distributed on two sides of the clamp arm in its axial direction at same positions in opposite tooth shapes.

19. A medical device for hemostasis or closure of tissues, said medical device comprising:
a handle;
a sheath device, which is attached to the handle;
a clamp device comprising at least or exactly two clamp arms and a clamp housing with a clamp base, wherein the clamp base is in particular in a form of a sleeve provided on the distal end of the sheath device, and;

a control wire extending through the sheath device and configured to be reversibly movable in distal and proximal directions; and an actuator coupled to a proximal end of the control wire and configured to be actuable to reversibly move the control wire in the distal and proximal directions, wherein the clamp arms are each coupled to a distal end of the control wire and wherein the clamp device is configured to be actuable to open and close the clamp arms by a movement of the control wire such that a movement of the control wire in the proximal direction is translated into a closing movement of the clamp arms and a movement of the control wire in the distal direction is translated into an opening movement of the clamp arms, in particular according to claim 1, wherein the clamp device comprises:

exactly two clamp arms which are provided as separate elements, that are each coupled to the distal end of the control wire in a pivotal manner around a common pivot axis defined by a pivot pin, wherein each clamp arm is provided with a guide groove and the guide grooves of the two clamp arms partially overlap each other, and a guide pin, which is attached to the clamp housing and extends through the guide grooves in the overlapping parts thereof, so that by engagement of the guide pin and the guide grooves, a movement of the control wire in the proximal direction is translated into a closing movement of the clamp arms and a movement of the control wire in the distal direction is translated into an opening movement of the clamp arms around the pivot axis.

20. The medical device according to claim 19, wherein the guide pin is held between two bearing arms extending in the distal direction from the clamp housing, in particular at the free end sections of the bearing arms.

21. The medical device according to claim 19, wherein holding noses are provided on the clamp arms, the holding noses extending into the guide grooves from a lateral side thereof and being designed in such a way, that they allow the guide pin to pass them to reach the distal ends of the guide grooves but prevent passing of the guide pin in the opposite direction, wherein, in particular, the guide grooves have a straight, axially extending distal end section, in which the guide pin can move without incurring rotation of the clamp arms and the holding noses extend into the straight distal end sections.

22. The medical device according to claim 21, wherein recesses are formed in the lateral sides of the guide grooves on the distal side of the holding nose, into which the holding noses are elastically deformed to allow the guide pin to pass the holding noses and reach its distal end position in the guide grooves.

23. The medical device according to claim 19, wherein each of the clamp arms is provided with at least two lateral teeth, wherein the at least two lateral teeth on the clamp arm on either side are distributed on two sides of the clamp arm in its axial direction at same positions in opposite tooth shapes.

* * * * *